United States Patent [19]
Tam

[11] Patent Number: 6,063,772
[45] Date of Patent: *May 16, 2000

[54] SPECIFIC MODULATION OF TH1/TH2 CYTOKINE EXPRESSION BY RIBAVIRIN IN ACTIVATED T-LYMPHOCYTES

[75] Inventor: Robert C. Tam, Costa Mesa, Calif.

[73] Assignee: ICN Pharmaceuticals, Inc., Costa Mesa, Calif.

[*] Notice: This patent is subject to a terminal disclaimer.

[21] Appl. No.: 09/097,450

[22] Filed: Jun. 15, 1998

Related U.S. Application Data

[63] Continuation of application No. 08/590,449, Jan. 23, 1996, Pat. No. 5,767,097.

[51] Int. Cl.[7] .................. A61K 31/495; C07H 19/167

[52] U.S. Cl. .................. 514/43; 514/2; 514/23; 514/27; 514/46; 536/28.6; 536/28.7; 536/29.1

[58] Field of Search .................. 514/43, 46, 2, 514/23, 27; 536/28.6, 29.1, 28.7

[56] References Cited

PUBLICATIONS

Abonyi, M, et al, Comparative Efficacy of 6 Months Treatment with Interferon Alfa–2b, Ribavirin and Combination Therapy in Chronic Hepatitis C, *Progress in Hepato–Pharmacology*, 1995, 1:254–261.

Di Bisceglie, AM, et al, A Pilot Study of Ribavirin Therapy for Chronic Hepatitis C, *Hepatology* 1992, 16:649–654.

Di Bisceglie, AM, et al, Randomized, Double Blind Placebo–Controlled Trial of Ribavirin Therapy for Chronic Hepatitis C, *Hepatology*, 1993, 18:145.

Di Bisceglie, AM, et al, Randomized, Double Blind Placebo–Controlled Trial of Ribavirin Therapy for Chronic Hepatitis C, *Annals of Internal Medicine*, 1995, 123:897–903.

Bizollon, T, et al, Ribavirin and Interferon Treatment for Hepatitis C Recurrence Following Orthopic Liver Transplantation, Abstract from the 29th Annual Meeting of the European Association for the Study of the Liver, Sep. 7–10, 1994.

Bizollon, T, et al, New Approaches to the Treatment of Hepatitis C Virus Infection After Liver Transplantation Using Ribavirin, *J. of Hepatology*, 1995, 23(2):22–25.

Bodenheimer Jr, et al, Tolerance and Efficacy of Oral Ribavirin Treatment of Chronic Hepatitis C: A Multicenter Trial, 1994.

Braconier, JH, et al, Combined Alpha–Interferon And Ribavirin Treatment in Chronic Hepatitis C: A Pilot Study, *Scand J Infect Dis*, 1995, 27: 325–329.

Brillanti S, et al, Combination Therapy With Ribavirin and α–Interferon in Patients with Chronic Hepatitis C . . . , AASLD Abstract, 1993.

Brillanti S, et al, A Pilot Study Of Combination Therapy With Ribavirin Plus Interferon Alfa for Interferon Alfa–Resistant Chronic Hepatitis C, *Gastroenterology*, 1994:107, 812–817.

Brillanti, S, et al, Combination Antiviral Therapy With Ribavirin And Interferon Alfa In Interferon Alfa Relapsers And Non Responders: Italian Experience, *Journal of Hepatology*, 1995: 23 (2): 13–16.

Brouwer, JT, et al, What Options Are Left When Hepatitis C Does Not Respond to Interferon? Placebo–Controlled Benelux Multicentre Retreatment Trial on Ribavirin Monotherapy Versus Combination with Interferon, Abstract from the Following Orthopic Liver Transplantation, Abstract from the 29th Annual Meeting of the European Association for the Study of the Liver, Sep. 7–10, 1994.

Camps, J, et al, Ribavirin in the Treatment of Chronic Hepatitis C Unresponsive to Alpha Interferon, *J. of Hepatology* 1993, 19:408–412.

Cattral M, New Approaches to Treatment of Hepatitis C in Transplant Patients and the Canadian Experience, Therapeutic Challenges in HCV: A Symposium During the American College of Gastroenterology Annual Meeting, Sep. 29, 1994, San Francisco Marriott.

Chemello, L, et al, Response to Ribavirin to Interferon and to a Combination of Both in Patients with Chronic Hepatitis C and its Relation to HCV Genotypes, Abstract from the 29th Annual Meeting of the European Association for the Study of the Liver, Sep. 7–10, 1994.

Chemello, L, et al., The Effect of Interferon Alfa and Ribavirin Combination Therapy in Naive Patients with Chronic Hepatitis C, *J. of Hepatology*, 1995, 23:(2)8–12.

Chossegros, P, et al, In Kidney Graft Recipients Ribavirine Is Able To Reduce HCV Viral Load, (*Journal unknown*), (date unknown).

Dieterich, DT, et al, Use Of Ribavirin For Recurrent Hepatitis C Virus (HCV) In Liver Transplant Patients After Failure Of Interferon, Abstract Form From American Gastroenterological Association And American Association For The Study Of Liver Diseases, New Orleans, Louisiana, May 15–18, 1994.

Dusheiko, G, et al, Ribavirin Treatment for Patients with Chronic Hepatitis C: Results of a Placebo–Controlled Study, *J. of Hepatology*, 1996, 25:591–598.

(List continued on next page.)

*Primary Examiner*—James O. Wilson
*Assistant Examiner*—Howard Owens
*Attorney, Agent, or Firm*—Fish & Associates; Robert D. Fish

[57] ABSTRACT

Ribavirin is administered to a patient in a dosage range which is effective to modulate lymphokine expression In activated T cells. In particular, ribavirin is used to suppress Th2-mediated T cell responses and promote Th1-mediated T cell response. Thus, instead of administering ribavirin in its well-recognized role as an anti-viral agent, ribavirin is herein used in the treatment of imbalances in lymphokine expression. Such imbalances may be found to be concomitants of allergic atopic disorders such as allergic asthma and atopic dermatitis, helminth Infection and leishmaniasis, and various primary and secondary immunodeficiencies, which may or may not also be associated with viral infection.

9 Claims, 7 Drawing Sheets

OTHER PUBLICATIONS

Dusheiko, G, et al, Results Of A Placebo–Controlled Study Of Ribavirin In Patients With Chronic Hepatitis C, Abstract From The 45th Annual Meeting Of The American Association For The Study Of Liver Diseases, Oct. 1994, 440.

El–Zayadi, A, et al, Combination Treatment of Alpha Interferon–2b (alpha IFN) and Ribavirin in Chronic Hepatitis C Genotype 4 Patients Resistant to Interferon Therapy, *Hepatology*, Abstracts, Oct. 1995, 182.

Gane et al, Ribavirin Therapy for Hepatitis C Infection Following Liver Transplantation, *Transpl. Int.* 1995, 8:61–64.

Gatell JM, et al, Efficacy of Ribavirin on Hepatitis C Virus Infection in HIV Infected Patients, Abstract from the 32nd ICAAC, Oct. 1992, Anaheim, California.

Grellier, L, et al, CD4 Positive T Lymphocyte Proliferative Responses In A Cohort Of Patients With Chronic Hepatitis C Virus Treated With Ribavirin and Interferon, Hepatology, Oct. 1997, Abstract 1112.

Hoofnagle, JH, et al, Long–Term Therapy with Ribavirin for Chronic Hepatitis C, Abstract Form for Third International Meeting on Hepatitis C Virus and Related Viruses, Marriott Surfers Paradise Resort, Gold Coast Australia, Aug. 28–Sep. 3, 1995.

Hoofnagle, JH et al, Abstract, Abstract From $3^{rd}$ Int'l Meeting on Hepatitis C Virus and Related Viruses, 1995.

Hultgren, C, et al, Ribavirin Therapy Shifts the T–Helper 1 (TH1)/TH2 Subset Balance in Vivo, Gastroenterologie Clinique & Biologique: Abstracts Book, (92), Vth International Conference Current Trends in Chronically Evolving Viral Hepatitis, Oct. 1997, Lyon, France.

Kakumu, S, et al, A Pilot Study of Ribavirin and Interferon Beta for the Treatment of Chronic Hepatitis C, *Gastroenterology*, 1993, 105:507–512.

Koskinas, J, et al, Effects of Ribavirin on Intra– and Extra–Hepatic Replication of Hepatitis C Virus in Interferon.

Non–Responsive tients, International Symposium on Viral titis, Madrid Spain, Feb., 1994.

Lai, M, et al, Combination Therapy of a–Interferon and Ribavirin in Patients with Chronic Hepatitis C: An Interim Report, *AASLD Abstracts 93A,* Chicago, Nov. 4–7, 1993 (146).

Lai, M, et al, Long–term Efficacy of Ribavirin Plus Interferon Alfa in the Treatment of Chronic Hepatitis C, *Gastroenterolgy,* 1996, 111:1307–1312.

Lechmann et al, T– and B–Cell Responses to Different Hepatitis C Virus Antigens . . . , *Hepatology* 1996, 24:790–795.

Ljungman, P, et al, Oral Ribavirin for Prevention of Severe Liver Disease Caused by Hepatitis C Virus During Allogeneic Bone Marrow Transplantation, *Clinical Infectious Diseases,* 1996, 23:167–169.

Martin et al, Effect of Ribavirin on Peripheral Blood Mononuclear Cells (PBMC) in Patients with Chronic Hepatitis C, *Hepatology* 1996, 24:394A.

Naoumov, N.V, Host Immune in Responses in Chronic HCV Infection, Gastroenterologie Clinique & Biologique: Abstracts Book 1997, (145) Vth International Conference Current Trends in Chronically Evolving Viral Hepatitis, Oct. 1997, (92) Lyon, France.

Nelson, D, et al, Intrahepatic Hepatitis C Virus–Specific Cytotoxic T Lymphocyte Activity and Response to Interferon Alfa Therapy in Chronic Hepatitis C, *Hepatology,* 1998, 28:225–230. (Abstract published in 1997).

Ning, Q, et al, Ribavirin Inhibits Viral Induced Macrophage Production of Tumor Necrosis Factor . . . , *Hepatology* 1996, 24:335A. (abstract published in 1996).

Pol, S, et al, Ribavirin–Interferon vs Interferon (a2b–IFN) Alone in Non–Responders to a–IFN in Chronic Hepatitis C, *Hepatology* Abstracts, Oct. 1996, (918).

Reichard, O, et al, Ribavirin Treatment for Chronic Hepatitis C, *Lancet* 1991, 337:1058–91.

Reichard, O, et al, Hepatitis C Viral RNA Titers in Serum Prior to, During, and After Oral Treatment with Ribavirin for Chronic Hepatitis C, *Journal of Medical Virology,* 1993, 41:99–102.

Reziez, M, et al, Treatment of Hepatitis C Viral Infection (HCV) in the Transplanted Patient with Ribavirin, Abstract from the 44th Annual Meeting of the American Association for the Study of Liver Diseases, Oct. 1993 (1144).

Salmerón et al, Interferon Versus Ribavirin Plus Interferon in Chronic Hepatitis C . . . , *Hepatology,* 1996, 24:394.

Tagger, A, et al, Quantitation And Typing Of Hepatitis C Virus RNA In Patients On Interferon And Ribavirin Prophylaxis After Liver Transplantation; 4th International Symposium On Hepatitis C Virus And Related Viruses (Molecular Virology And Pathogenic); Surfers Paradise Resort Gold Coast Australia, Aug. 28–Sep. 3, 1995.

Tripi, S. et al, Ribavirin Plus Alfa B Interferon and Ribavirin Alone in Resistant Chronic Hepatitis C, *Hepatology* AASLD Abstract, 1996, 24 (1857).

Weiland O, et al, Combination Treatment with Interferon Alpha–2b and Ribavirin in Patients Suffering from Chronic Hepatitis C Relapsing After, or Not Responding to Earlier Treatment with Interferon, Translation of Abstract from *Läkarstämman* (Swedish Physician's Meeting) Stockholm, Dec. 1993.

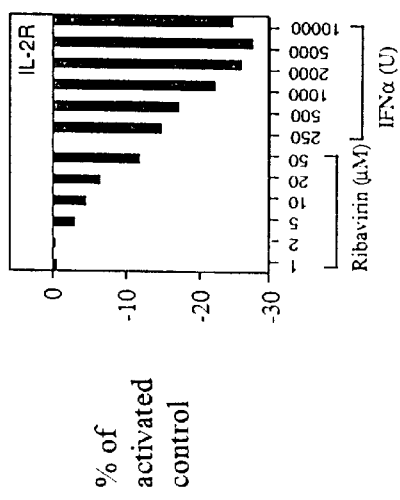 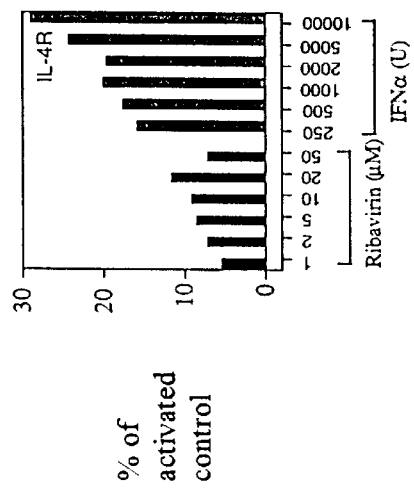
Figure 4A  Figure 4B
FIGURE 4

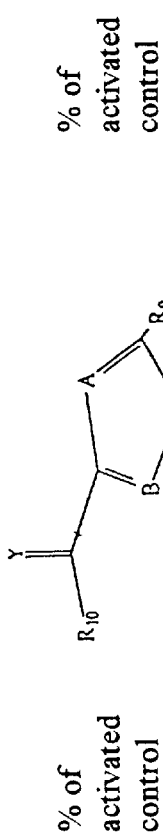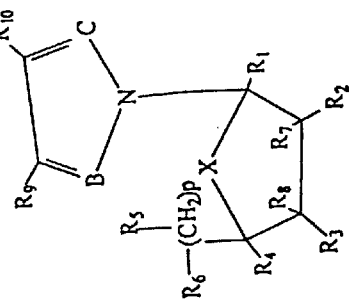
Figure 6B
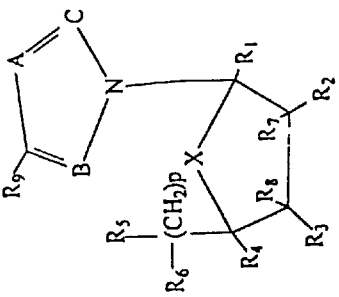
Figure 6D
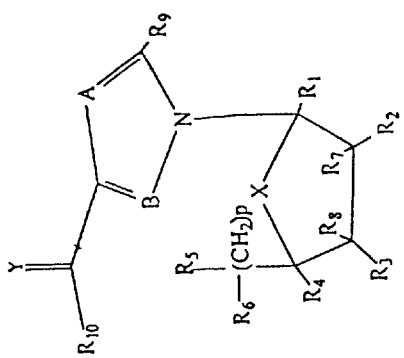
Figure 6A
Figure 6C

SPECIFIC MODULATION OF TH1/TH2 CYTOKINE EXPRESSION BY RIBAVIRIN IN ACTIVATED T-LYMPHOCYTES

This application is a continuation of application Ser. No. 08/590,449 filed Jan. 23, 1996, issued as U.S. Pat. No. 5,767,097.

FIELD OF THE INVENTION

The field of the invention is immunology.

BACKGROUND OF THE INVENTION

The lymphokines are a group of polypeptides belonging to the family of cytokines, i.e. hormone-like molecules that can affect various cell functions and enable communication between different cells. Recent developments have helped to clarify the role of lymphokines in the immune response. Lymphokine production by helper $CD4^+$ (and also in $CD8^+$) T cells frequently fall into one of two phenotypes, Th1 and Th2, in both murine and human systems (Romagnani, 1991, *Immunol Today* 12:256–257, Mosmann, 1989, *Annu Rev Immunol*, 7:145–173). Th1 cells produce interleukin 2 (IL-2), tumor necrosis factor (TNFα) and interferon gamma (IFNγ) and they are responsible primarily for cell-mediated immunity such as delayed type hypersensitivity. Th2 cells produce interleukins, IL4, IL-5, IL-6, IL-9, IL-10 and IL-13 and are primarily involved in providing optimal help for humoral immune responses such as IgE and IgG4 antibody isotype switching (Mosmann, 1989, *Annu Rev Immunol*, 7:145–173).

Strongly polarized Th1 and Th2 responses not only play different roles in protection, they can promote different immunopathological reactions. Th1-type responses are involved in organ specific autoimmunity such as experimental autoimmune uveoretinitis (Dubey et al, 1991, *Eur Cytokine Network* 2:147–152), experimental autoimmune encephalitis (EAE) (Beraud et al, 1991, *Cell Immunol* 133:379–389) and insulin dependent diabetes mellitus (Hahn et al, 1987, *Eur J Immunol* 18:2037–2042), in contact dermatitis (Kapsenberg et al, *Immunol Today* 12:392–395), and in some chronic inflammatory disorders. In contrast Th2-type responses are responsible for triggering allergic atopic disorders (against common environmental allergens) such as allergic asthma (Walker et al, 1992, *Am Rev Resp Dis* 148:109–115) and atopic dermatitis (van der Heijden et al, 1991, *J Invest Derm* 97:389–394), are thought to exacerbate infection with tissue-dwelling protozoa such as helminths (Finkelman et al, 1991, *Immunoparasitol Today* 12:A62–66) and Leishmania major (Caceres-Dittmar et al, 1993, *Clin Exp Immunol* 91:500–505), are preferentially induced in certain primary immunodeficiencies such as hyper-igE syndrome (Del Prete et al, 1989, *J Clin Invest* 84:1830–1835) and Omenn's syndrome (Schandene et al, 1993, *Eur J Immunol* 23:56–60), and are associated with reduced ability to suppress HIV replication (Barker et al, 1995, *Proc Soc Nat Acad Sci USA* 92:11135–11139).

Thus, it is clear that modulation of the lymphokine profiles of the is aforementioned disease states would be of therapeutic benefit. Promoting a Th1 response would most likely lead to the reversal of a Th2 phenotype and vice versa. Monoclonal antibodies (mAb) to lymphokines, lymphokines themselves and other agents such as thiol antioxidants (Jeannin et al, 1995, *J Exp Med* 182:1785–1792) have been shown to reverse the pathogenesis of certain diseases by inhibiting the disease-promoting cytokine pattern, either Th1 or Th2. For example, intracellular protozoan infections are limited by IFNγ but exacerbated by IL4, while nematode infections are controlled by IL-4 and exacerbated by IFNγ (Heinzel et al, 1989, *J Exp Med* 162:59–72, Else et al, 1994, *J Exp Med* 179:347–351). Insulin-dependent diabetes mellitus in NOD mice and EAE in mice and rats can be ameliorated by treatment with IL-4 or anti-IFNγ mAb before development of the disease (Rapoport et al, 1993, *J Exp Med* 178:87–99, Racke et al, 1994, *J Exp Med* 180:1961–1966, Campbell et al, 1991, *J Clin Invest* 87:739–742). In addition, autoimmune graft versus host disease (GVHD) that is characterized by a systemic lupus erythrematosus-like syndrome is associated with Th2 lymphokine production and is inhibited by anti-IL-4 antibody (Umland et al, 1992, *Clin Immunol Immunopathol* 63:66–73). On the other hand, Th1 cytokines are produced in acute GVHD, in which donor $CD8^+$ T cells develop into CTL and destroy the host immune system. Treatment with anti-IFNγ or anti-TNFα mAb ameliorates disease, and treatment with anti-IL-2 mAb converts acute GVHD to autoimmune GVHD (Via and Finkelman, 1993, *Int Immunol* 5:565–572).

Clinical trials of native and recombinant IL-2 in treating HIV-infected patients have been in progress since 1983 (Volberding et al, 1987, *AIDS Res Hum Retroviruses*, 3:115–124). Here, the relationship comes from the fact that development of AIDS has been reported to be associated with a shift in the pattern of lymphokines produced (Clerici and Shearer, 1994, *Immunol Today* 15:575–581). Over time, in an infected individual progressing towards disease, a decreased expression of Th1 lymphokines such as IL-2 occurs (Maggi et al, 1987, *Eur J Immunol* 17:1685–1690, Gruters et al, 1990, *Eur J Immunol* 20:1039–1044, Clerici et al, 1993, *J Clin Invest* 91:759–765), concomitant with an increased production of Th2 lymphokines such as IL-4 and IL-10 (Clerici et al, 1994, *J Clin Invest* 93:768–775, Hoffman et al, 1985, *Virology* 147:326–335). T-cells from asymptomatic or long term survivors treated with IL-2 enhanced their anti-HIV activity whereas exposure to IL-4 or IL-10 reduced their ability to suppress HIV replication and to produce IL-2 (Barker et al, 1995, *Proc Soc Nat Acad Sci USA* 92:11135–11139).

These current immunomodulatory therapeutics (mAbs and recombinant cytokines) are, however, not without limitations. For example with chronic monoclonal antibody treatment, the host animal develops antibodies against the monoclonal antibodies thereby limiting their usefulness. 'Humanized' monoclonal antibodies have been developed which apparently reduces the risk of an induced immune response to these mAbs. However, these are still under development, and in addition these new mAbs remain large proteins and therefore may have difficulty reaching there target sites. Cytokine-based therapeutics also have limitations. For example, IL-12 treatment of autoimmune GVHD leads to the development of acute GVHD in mice.

Ribavirin (1-β-D-ribofuranosyl-1,2,4-triazole-3-carboxamide) is a synthetic nucleoside capable of inhibiting RNA and DNA virus replication (Huffman et al, 1973, *Antimicrob. Agents Chemother* 3:235, Sidwell et al, 1972, *Science* 177:705). We have confirmed the observations of others who suggested that ribavirin, in addition to its antiviral activity, has an effect on certain immune responses (reviewed Jolley and Suchil, 1984, *Clinical Applications of Ribavirin: p*93–96). We have also confirmed observations of others that ribavirin affects the proliferation of mitogen- and antigen-activated T and B lymphocytes, (Tam et at, 1995 (data not shown), Peavy et al, 1980, *Infection and Immunity* 29:583–589) and then when combined with cyclosporin, ribavirin showed efficacy in long term allograft survival , Jolley et al (1988, *Transplantation Proc* 20:703–706).

In addition, we have significantly advanced the prior research by demonstrating that ribavirin modulates the cytokine pattern of an immune response at least in part by promoting a Th1 response and suppressing a Th2 response. In hindsight, this discovery is not inconsistent with prior research. First, ribavirin is known to inhibit both functional humoral immune responses, (Peavy et al, 1981, *J Immunol* 126:861–864, Powers et al, 1982, *Antimicrob Agents Chemother* 22:108–114) and IgE-mediated modulation of mast cell secretion (Marquardt et al, 1987, *J Pharmacol Exp Therapeutics* 240:145–149, (both Th2 lymphokine-mediated events). Second, ribavirin antagonizes the antiviral effect of azidothymidine (AZT) in peripheral blood lymphocytes from HIV patients (Vogt et al, 1987, *Science* 235:1376–1379). This finding is significant because AZT decreases IL-2 receptor (IL-2R) but not IL-2 expression (Viora and Camponeschi, 1995, *Cell Immunol* 163:289–295). It is therefore possible that ribavirin antagonizes AZT by modulating IL-2 expression and elevating depressed levels of IL-2R. Third, ribavirin treatment of an immunocompromised patient for chronic GVHD (a Th2-mediated disorder) led to a dramatic resolution of the disease, an outcome which did not occur with conventional immunosuppressive therapies such as cyclosporin and glucocorticoids (Cassano, 1991, *Bone Marrow Transplantation* 7:247–248). Finally, ribavirin treatment (one year) of patients for hepatitis C (HCV) revealed fewer lymphocyte aggregates and far less liver damage than placebo controls (Dusheiko et al, 1994, *Hepatology* 20:206A). This observation may reflect the fact that although, the predominant immune response to hepatitis C is mediated by Th1 lymphokines, T cells of the Th0/Th2 phenotype can be infected by HCV (Zignego et al, 1994, unpublished data) and this infection may drive further antibody-mediated destruction of hepatocytes.

BRIEF DESCRIPTION OF THE DRAWINGS

FIG. 4A is a graphical representation of the effect of Ribavirin and interferon alpha on the cell surface expression of IL-2 receptors in PMA/ionomycin-activated T lymphocytes. Results are expressed as percentage of the increased lymphokine receptor expression following PMA/ionomycin treatment alone.

FIG. 4B is a graphical representation of the effect of Ribavirin and interferon alpha on the cell surface expression of IL-4 receptors in PMA/ionomycin-activated T lymphocytes. Results are expressed as percentage of the increased lymphokine receptor expression following PMA/ionomycin treatment alone.

FIG. 6A is a graphical representation of a contemplated Ribavirin analog.

FIG. 6B is a graphical representation of a contemplated Ribavirin analog.

FIG. 6C is a graphical representation of a contemplated Ribavirin analog.

FIG. 6D is a graphical representation of a contemplated Ribavirin analog.

SUMMARY OF THE INVENTION

Figure 1:
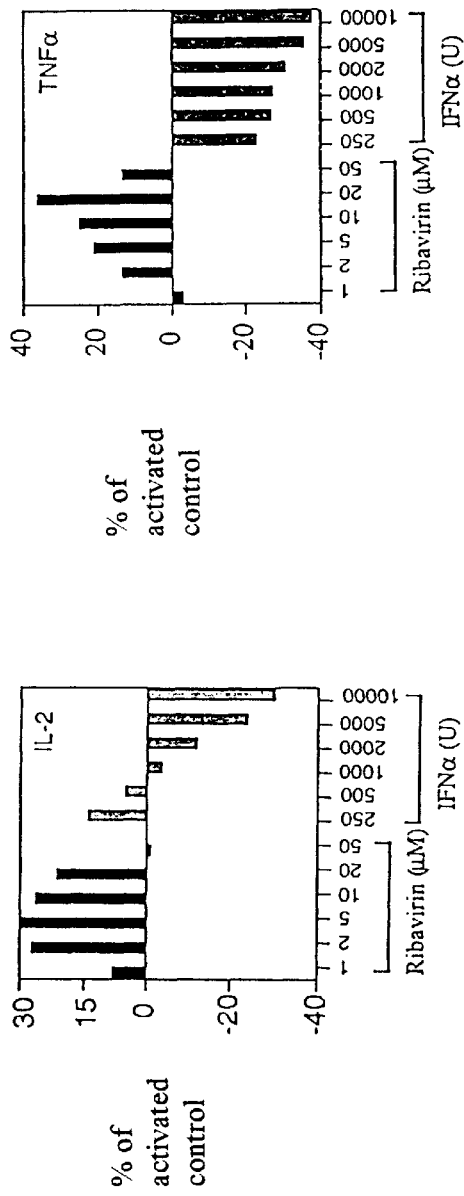
FIG. 1A is a graphical representation of the effect of Ribavirin and interferon alpha on the extracellular expression of IL-2 in PMA/ionomycin-activated T lymphocytes. Results are expressed as percentage of the increased lymphokine expression following PMA/ionomycin treatment alone.
FIG. 1B is a graphical representation of the effect of Ribavirin and interferon alpha on the extracellular expression of TNFα in PMA/ionomycin-activated T lymphocytes. Results are expressed as percentage of the increased lymphokine expression following PMA/ionomycin treatment alone.
FIG. 1C is a graphical representation of the effect of Ribavirin and interferon alpha on the extracellular expression of IL-4 in PMA/ionomycin-activated T lymphocytes. Results are expressed as percentage of the increased lymphokine expression following PMA/ionomycin treatment alone.
FIG. 1D is a graphical representation of the effect of Ribavirin and interferon alpha on the extracellular expression of IFNγ in PMA/ionomycin-activated T lymphocytes. Results are expressed as percentage of the increased lymphokine expression following PMA/ionomycin treatment alone.
Figure 1:
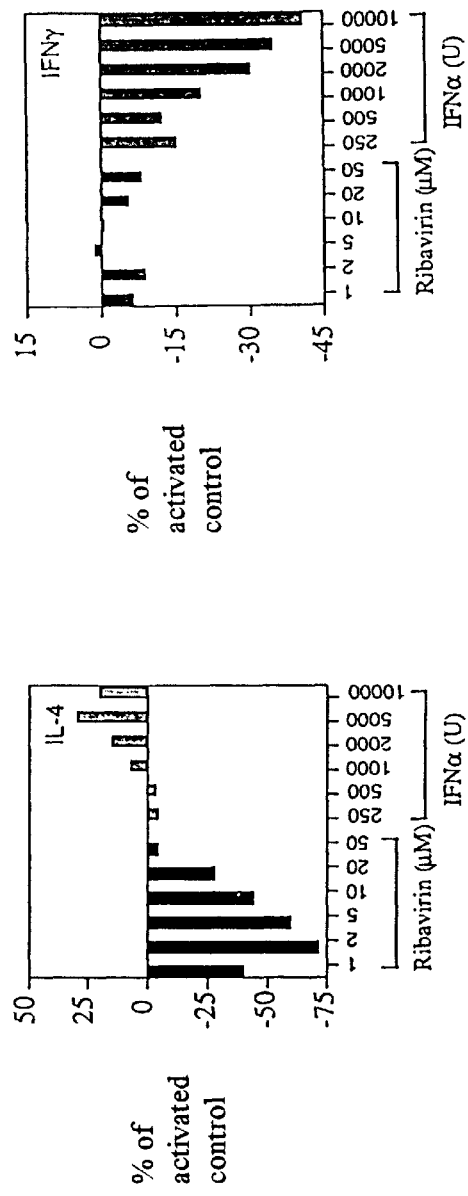

In accordance with the present invention, the nucleoside, ribavirin, is administered to a patient in a dosage range which is effective to modulate lymphokine expression in activated T cells. In particular, ribavirin is used to suppress Th2-mediated T cell responses and promote Th1-mediated T cell response.

Thus, instead of administering ribavirin in its well-recognized role as an anti-viral agent, ribavirin is herein used in the treatment of imbalances in lymphokine expression. Such imbalances may be found to be concomitants of allergic atopic disorders such as allergic asthma and atopic dermatitis, helminth infection and leishmaniasis, and various primary and secondary immunodeficiencies, which may or may not also be associated with viral infection.

DETAILED DESCRIPTION OF SPECIFIC EMBODIMENTS

In a preferred embodiment, ribavirin is administered orally to a human patient in a dosage which achieves a blood serum level averaging 0.25–12.5 µg/ml, and most preferably, approximately 2.5 µg/ml. In a typical individuals, this optimimum serum level, works out to be approximately 4.5 mg/kg/day of body weight which can be administered in doses from 200–1200 mg. Preferably the dosages are divided into a number of smaller doses which are then administered throughout the day.

Since ribavirin has been on the market for several years, many dosage forms and routes of administration are known, and all appropriate dosage forms and routes of administration may be utilized. For example, in addition to oral administration, ribavirin may given intravenously, intramuscularly, intraperitoneally, topically, and the like, all of which are known. Pharmaceutical formulations comprising ribavirin may also comprise one or more pharmaceutically acceptable carrier, which may include excipients such as stabilizers (to promote long term storage), emulsifiers, binding agents, thickening agents, salts, preservatives, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the ribavirin, its use in the therapeutic compositions and preparations is contemplated. Supplementary active ingredients can also be incorporated into the compositions and preparations.

In addition to the therapeutic uses of the ribavirin contemplated herein, ribavirin may also be used as a laboratory tool for the study of absorption, distribution, cellular uptake, and efficacy.

EXAMPLES

Cell Lines And T Cell Purification

Peripheral blood mononuclear cells (PBMCs) were isolated from the buffy coat following Ficoll-Hypaque density gradient centrifugation of 60 ml blood from healthy donors. T-cells were then purified from the PBMCs using Lymphokwik lymphocyte isolation reagent specific for T-cells (LK-25T, One Lambda, Canoga Park Calif.). An average yield of 40–60×10$^6$ T-cells were then incubated overnight at 37° C. in 20–30 ml RPMI-AP5 (RPMI-1640 medium ICN, Costa Mesa, Calif.) containing 20 mM HEPES buffer, pH 7.4, 5% autologous plasma, 1% L-glutamine, 1% penicillin/streptomycin and 0.05% 2-mercaptoethanol) to remove any contaminating adherent cells. In all experiments, T-cells were washed with RPMI-AP5 and then plated on 96-well microtitre plates at a cell concentration of 1×10$^6$ cells/mi.

T-Cell Activation And Ribavirin Treatment

T-cells were activated by the addition of 500 ng ionomycin and 10 ng phorbol 12-myristate 13-acetate (PMA) (Calbiochem, La Jolla, Calif.) and incubated for 48–72 h at 37° C. PMA/ionomycin-activated T-cells were treated with 0.5–50 µM ribavirin or with 250–10000 U/ml of a control antiviral, interferon-alpha (Accurate, Westbury, N.Y.) immediately following activation and re-treated 24 h later. T-cells from each plate were used for immunofluorescence analysis and the supernatants used for extracellular cytokine measurements. Following activation, 900 µl cell supernatant from each microplate was transferred to another microplate for analysis of cell-derived cytokine production. The cells are then used in immunofluorescence analyses for intracellular cytokine levels and cytokine receptor expression.

Extracellular Cytokine Analyses

Cell-derived human cytokine concentrations were determined in cell supernatants from each microplate. Activation-induced changes in interleukin-2 (IL-2) levels were determined using a commercially available ELISA kit (R & D systems Quantikine kit, Minneapolis, Minn.) or by bioassay using the IL-2-dependent cell line, CTLL-2 (ATOC, Rockville, Md.). Activation-induced changes in interleukin-4 (IL-4), tumor necrosis factor (TNF$\alpha$) interleukin-8 (IL-8) (R & D systems (Quantikine kit, Minneapolis, Minn.) and interferon-gamma (IFN-$\gamma$) (Endogen (Cambridge, Mass.) levels were determined using ELISA kits. All ELISA results were expressed as pg/ml and the CTLL-2 bioassay as counts per minute representing the IL-2-dependent cellular incorporation of $^3$H-thymidine (ICN, Costa Mesa, Calif.) by CTLL-2 cells.

Direct Immunofluorescence Studies (Cytokine Receptors)

For direct staining with fluorescence-conjugated antibodies to cell surface antigens, the cells were washed twice with isotonic saline solution, pH 7.4 (Becton Dickinson, Mansfield, Mass.) and resuspended in 50 μl isotonic saline solution and split into two samples. One sample aliquot was co-stained with either PE-anti CD25/FITC-anti CD4 or PE-rat anti mouse IgG+anti-CDw124/FITC-anti CD4 mAb and non-specific fluorescence was assessed by staining the second aliquot with PE/FITC-labeled isotype-matched control monoclonal antibody. All fluorescence-labeled monoclonal antibodies were obtained from Becton Dickinson (San Jose, Calif.) except for anti-CDw124 which was obtained from Pharmingen, San Diego, Calif. Incubations were performed at 4° C. in the dark for 45 min using saturating mAb concentrations. Unincorporated label was removed by washing in PBS prior to the analysis with a FACScan flow cytometer (Becton Dickinson).

Antigen density was indirectly determined in gated live $CD4^+$ T cells and expressed as the mean channel of fluorescence (MCF). Surface expression of specific antigen (CDw124, CD25) was represented as the mean channel shift (MCS) obtained by subtracting the MCF of FITC- or PE-labeled isotype-matched (IgG1) control mAb-stained cells from the MCF of FITC- or PE-labeled antigen-specific mAb stained cells. Alternatively, surface expression of the CD4+-subset of cells stained with CD28 mAb was determined by subtracting the MCF of CD28+ CD4+ from the MCF of CD28− CD4− cells.

The viability of control untreated and ribavirin and interferon a-treated cells were determined in each batch of all oligonucleotides in multiple donors by staining with the vital dye, propidium iodide (5 μg/ml final concentration). The percentage of live cells which excluded propidium iodide was determined by flow cytometry and was >90% (range 90–99 %) following treatment with all concentrations used.

Immunofluorescence Analyses of Intracellular Cytokine Expression

For analyses of the intracellular expression of IL-2 in $CD4^+$ and $CD8^+$ T cell subsets, T cells were first treated for the last 4 h of 48–72 h activation with 10 μg Brefeldin A (Gibco BRL, Gaithersburg, Md.) to minimize secretion of newly synthesized IL-2 into the extracellular milieu. Following activation, 900 μl cell supernatant from each microplate was transferred to another microplate for analysis of cell-derived cytokine production. Prior to direct staining (30 min, 4 C., in the dark) with FITC-conjugated antibodies to the cell surface antigens, CD4 and CD8, the cells were washed twice with isotonic saline solution, pH 7.4 and resuspended in 100–150 μl Staining Buffer (phosphate buffered saline, pH 7.4 containing 1% Fetal Calf Serum (FCS) (Hyclone, Logan, Utah) and 0.1% sodium azide), and split into two samples. Stained cells were washed in 1 ml Staining Buffer and cell pellet resuspended in 100 μl Fixation Buffer (4% paraformaldehyde in PBS) following aspiration of the supernatant. Fixed cells were kept at 4 C. for 20 mins, then washed in 1 ml Staining Buffer and cell pellet resuspended with mixing in 50 μl Permeabilization Buffer (0.1% saponin (ICN, Costa Mesa, Calif.) in PBS). Permeabilized cells were stained with PE-labeled IL-2 antibody for 30 min at 4 C. in the dark and then washed in 1 ml Permeabilization Buffer, resupended in 250 μl Staining Buffer prior to FACS analysis.

Analysis of Cytokine mRNA

Total RNA was extracted from resting T cells and from ribavirin and interferon α-treated and untreated activated T cells using a commercial variation of the guanidium thiocyanatel phenol extraction technique (Trizol reagent (GIBCO/BRL). RNA was washed with 70% ethanol and finally resuspended in 10 μl DEPC-treated water.

cDNA synthesis reaction was performed as per manufacturers instructions (Promega, Madion, Wis.). Briefly, 1 μg of total RNA was heated at 65° C. for 10 min and cooled on ice before combining with 2 μl 10X reverse transcription buffer (100 mM Tris HCl (pH 8.8), 500 mM KCl, 1% Triton X-100), 5 mM MgCl, 2 μl 10 mM dNTPs (1 mM each dNTP), 0.5 μl RNase inhibitor, 1 μl oligo $(dT)_{15}$ primer (0.5 μg/μg RNA) and 0.65 μl AMV reverse transcriptase (H. C.). The reaction was incubated at 42° C. for 1 h followed by at 95° C. for 10 min and 5 min on ice.

The PCR reaction was performed using GeneAmp PCR kit (Perkin-Elmer Cetus, Foster City, Calif.). In a fresh tube, RT reaction mixture (3 μl) was combined with 5 μl 10X PCR buffer ( 500 mM KCl, 100 mM Tris-HCl, pH 8.3, 15 mM $MgCl_2$ and 0.01% (w/v) gelatin), 1 μl 10 mM dNTPs and 1 U of Taq DNA polymerase. The primers used were as follows: interleukin-2, interleukin-4, interferon-γ (human) primers (Stratagene, La Jolla, Calif.) and pHE7 ribosomal gene. Amplification conditions were 45 sec at 94° C., 1 min at 57° C. and 2 min at 72° C. for 35 cycles, followed by 8 min at 72° C. PCR products were analyzed on 2% agarose gel containing ethidium bromide. Following electrophoresis, PCR products were transferred to Hybond N+ membrane (Amersham, Arlington Heights, Ill.) in 20X SSC overnight and immobilized using 0.4 M NaOH. Blots were hybridized with $^{32}P$-γATP labeled oligonucleotide probes in Rapid—hyb buffer (Amersham) for 1 h at 42° C. Each cytokine primer mix was used as a radiolabeled probe (as per instructions). Equivalent loading was assessed following hybridization with a probe generated from pHE7 sense primer. Washed blots were then analyzed using Phosphorlmager.

Effect of Ribavirin on Extracellular Cytokine Levels in Activated T Cells

Figure 2:
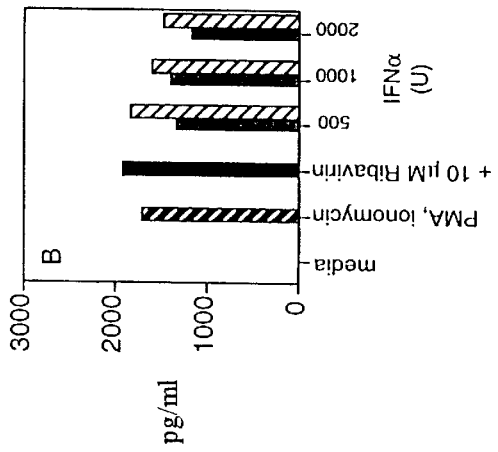
FIG. 2A is a graphical representation of the effect of 2, 10 or 50 $\mu$M Ribavirin in the presence of 2000 U/ml interferon alpha (left panels) and the effect of 500, 1000 or 2000 U/ml interferon alpha (right panels)in the presence of 10 $\mu$M Ribavirin on the extracellular expression of IL-2 in PMA/ionomycin-activated T lymphocytes.
FIG. 2B is a graphical representation of the effect of 2, 10 or 50 $\mu$M Ribavirin in the presence of 2000 U/ml interferon alpha (left panels) and the effect of 500, 1000 or 2000 U/ml interferon alpha (right panels)in the presence of 10 $\mu$M Ribavirin on the extracellular expression of IL-4 in PMA/ionomycin-activated T lymphocytes.
FIG. 2C is a graphical representation of the effect of 2, 10 or 50 $\mu$M Ribavirin in the presence of 2000 U/ml interferon alpha (left panels) and the effect of 500, 1000 or 2000 U/ml interferon alpha PMA/ionomycin-activated T lymphocytes.
FIG. 2D is a graphical representation of the effect 2, 10 or 50 $\mu$M Ribavirin in the presence of 2000 U/ml interferon alpha (left panels) and the effect of 500, 1000 or 2000 U/ml interferon alpha (right panels)in the presence of 10 $\mu$M Ribavirin on the extracellular expression of IL-4 in PMA/ionomycin-activated T lymphocytes.
Figure 2:
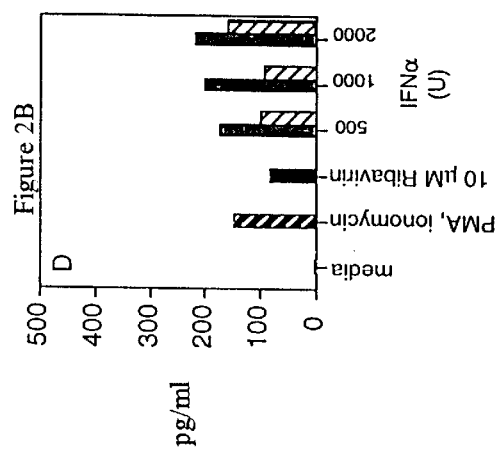
Figure 2:
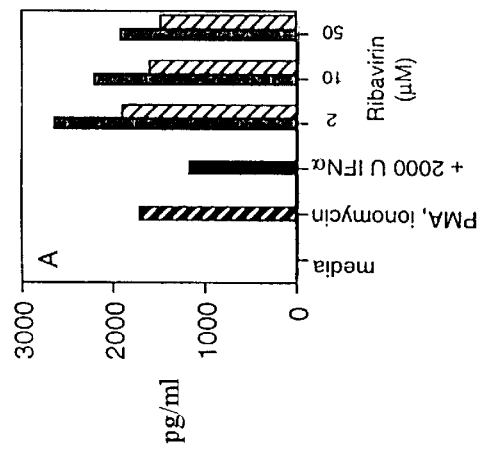
Figure 2:
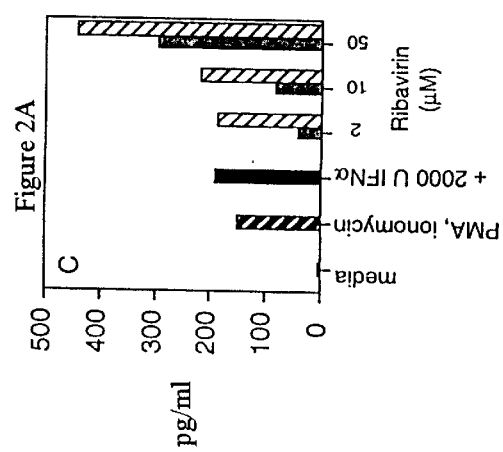

PMA/ionomycin treatment (48–72h) of human T-cells substantially increased the levels of all the cytokines analyzed i.e. IL-2, IL-4, TNFα, IFNγ (Table 1). The first number in each cell depicts the arithmetic mean, and the numbers in parenthesis depicts the relevant ranges. N=4. In a representative experiment shown in FIG. 1, addition of ribavirin, in the dose range 0.5–50 μM, augmented activated levels of the Th1 cytokines, IL-2 and TNFα maximally at 5 μM (30%) and 20 μM (36%) respectively. In contrast, interferon-α, inhibited IL-2 and TNFα expression in a dose-dependent manner (range 250–10000 U/ml, maximal inhibition 33 and 38% respectively), when compared to levels in untreated activated T cells. In addition, ribavirin mediated a concomitant decrease in activated levels of the Th2 cytokine, IL-4 (peak inhibition of 74% at 2 μM) whereas interferon-a maximally increased extracellular IL-4 by 26% (10000 U/ml). Using combinations of ribavirin and interferon alpha, FIG. 2 shows that a constant 2000 U/ml of interferon alpha suppressed the ribavirin dose-dependent augmentation of activated IL-2 levels (A) and reversed the inhibition of activated IL-4 levels (C). Similarly, a constant 10 μM of ribavirin reversed the interferon alpha-mediated dose-dependent inhibition of activated IL-2 levels (B) and suppressed the augmentation of activated IL-4 levels (D).

Effect of Ribavirin on Cytokine mRNA Levels In Activated T Cells

Figure 3:
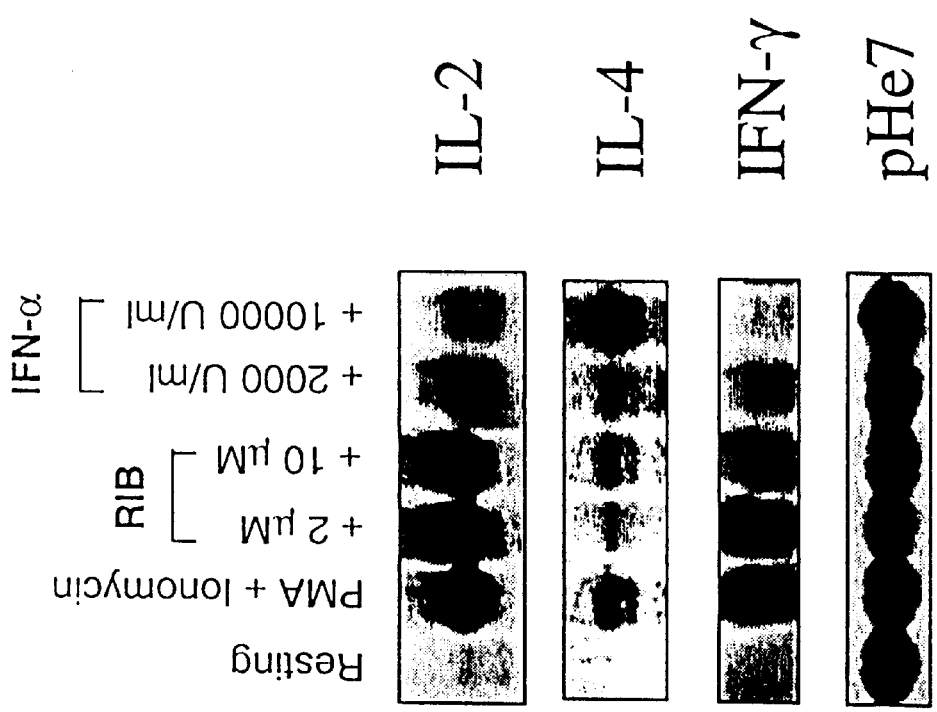
FIG. 3 is a graphical representation of the effect of Ribavirin and interferon alpha on IL-2, IL-4 and IFNγ mRNA expression in PMA/ionomycin-activated T lymphocytes.

These opposing effects of ribavirin and interferon-α on activated extracelfular cytokine levels were also observed at the level of transcription. FIG. 3 shows that PMA/ionomycin treatment of human T-cells substantially augments IL-2, IL-4 and IFNγ mRNA levels. Treatment with ribavirin (2, 5 and 10 μM) following T cell activation, elevates IL-2, decreases IL-4 and has no effect on IFNγ mRNA. In contrast, interferon α, at 1000, 2000 and 5000 U/ml decreases IL-2, increases IL-4 and decreases IFNγ mRNA. Therefore the respective dose-dependent effects of ribavirin and interferon α on IL-2, TNFα, and IL-4 mRNA expression paralleled the ELISA analyses. These data suggest that ribavirin promotes the synthesis of the Th1 cytokines, IL-2 and TNFα and inhibits the expression of the Th2 cytokine, IL-4 in activated human T cells Effect of Ribavirin on IL-2 and IL-4 Receptor Levels In Activated T Cells Using FACS analysis, we compared the effects of ribavirin and interferon α on expression of IL-2 (CD25) and IL-4 (CDw124) receptor expression in activated T cells. PMA/ionomycin-treatment increases CD25 and CDw124 expression from resting levels of 50.16±0.45 and 62.31±1.46 to activated levels of 162.48±2.89 and 87.53±3.98 respectively (n=4). In a representative of 3 experiments, FIG. 4 show that ribavirin (1–50 μM) has little effect on activated levels of IL-2 and IL-4 receptor whereas interferon a, in the dose range 250–10000 Ulml, decreased IL-2 receptor and increased IL-4 receptor expression in a dose-dependent manner, when compared to receptor levels in control activated T cells. Therefore, these data show that the effect of ribavirin on cytokine synthesis acts independently of cytokine receptor expression. In contrast, the effect of interferon a treatment on IL-2 and IL-4 receptor correlates with that observed with its effect on activated IL-2 and IL-4 expression.

Figure 5:
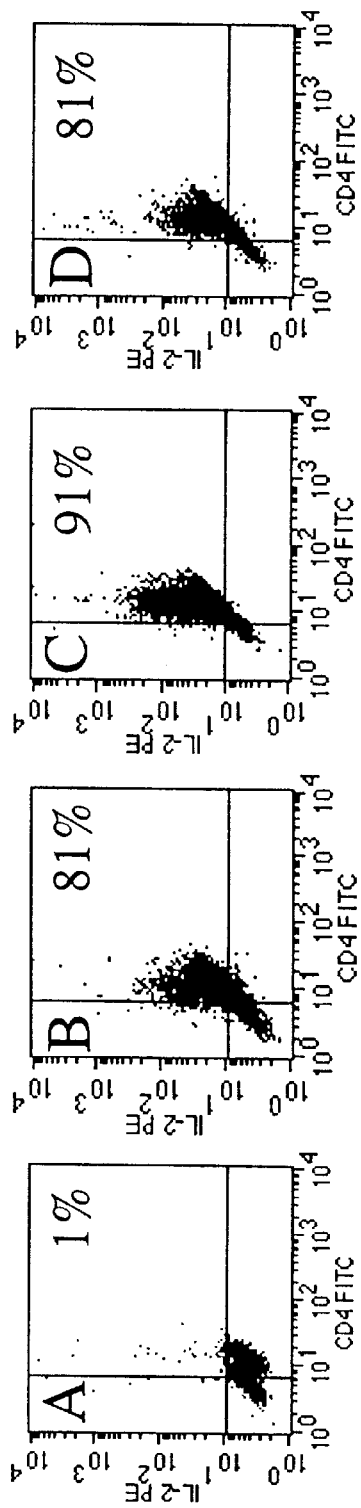
FIG. 5A is a graphical representation of the expression of intracellular IL-2 expression in resting CD4$^+$ T cells. Data form one experiment is shown and represented as the percentage of cells showing double positive staining for IL-2 and CD4 or CD8.
FIG. 5B is a graphical representation of the expression of intracellular IL-2 expression in activated CD4$^+$ T cells treated with PMA/ionomycin alone. Data from one experiment is shown and represented as the percentage of cells showing double positive staining for IL-2 and CD4 or CD8.
FIG. 5C is a graphical representation of the expression of intracellular IL-2 expression in activated CD4$^+$ T cells in the presence of 10 $\mu$M Ribavirin. Data from one experiment is shown and represented as the percentage of cells showing double positive staining for IL-2 and CD4 or CD8.
FIG. 5D is a graphical representation of the expression of intracellular IL-2 expression in activated CD4$^+$ T cells treated with 5000 U/ml interferon alpha. Data from one experiment is shown and represented as the percentage of cells showing double positive staining for IL-2 and Cd4 or Cd8.
FIG. 5E is a graphical representation of the expressio of intracellular IL-2 expression in resting CD8$^+$ T cells. Data from one experiment is shown and represented as the percentage of cells showing double positive staining for IL-2 and CD4 or CD8.
FIG. 5F is a graphical representation of the expression of intracellular IL-2 expression in activated CD8$^+$ T cells treated with PMA/ionomycin alone. Data from one experiment is shown and represented as the percentage of cells showing double positive staining for IL-2 and CD4 or CD8.
FIG. 5G is a graphical representation of the expression of intracellular IL-2 expression in activated CD8$^+$ T cells in the presence of 10 µM Ribavirin. Data from one experiment is shown and represented as the percentage of cells showing double staining for IL-2 and CD4 or CD8.
FIG. 5H is a graphical representation of the expression of intracellular IL-2 expression in activated CD8$^+$ T cells treatd with 5000 U/ml interferon alpha. Data from one experiment is shown and represented as the percentage of cells showing double positive staining for IL-2 and CD4 or CD8.
Figure 5:
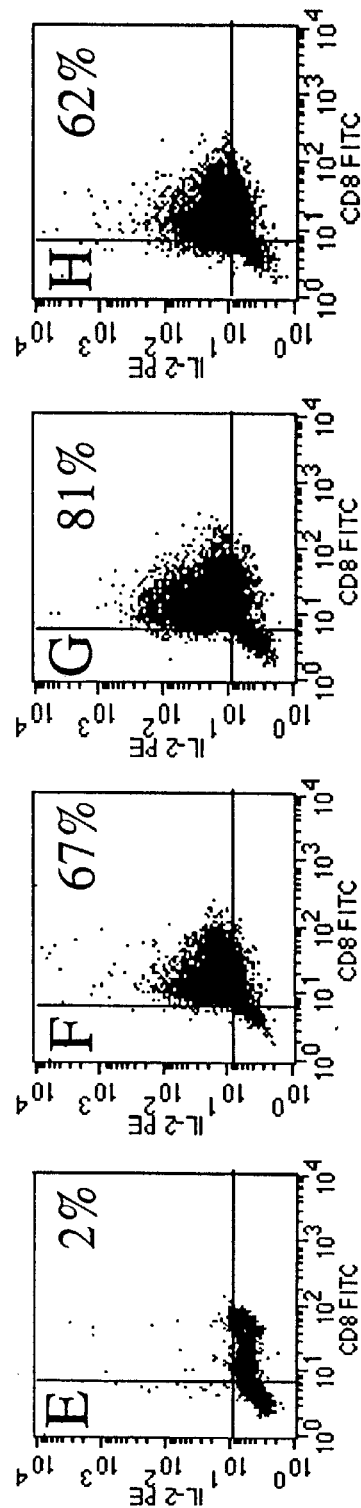
Figure 7C:
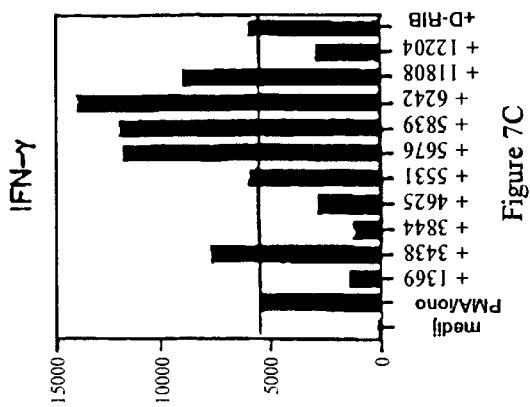
FIG. 7C is a graph showing the results of various concentrations of Ribavirin analogs on IFN-$\gamma$.
Figure 7B:
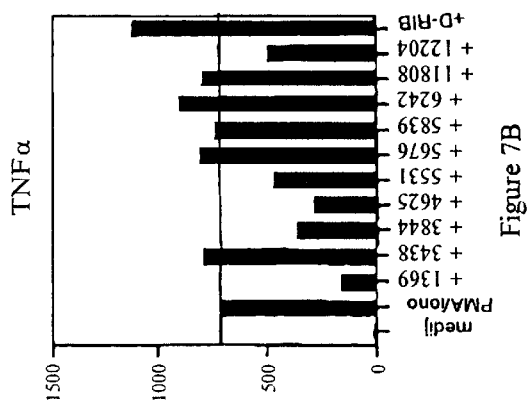
FIG. 7B is a graph showing the results of various concentrations of Ribavirin analogs on TNF-$\alpha$.
Figure 7E:
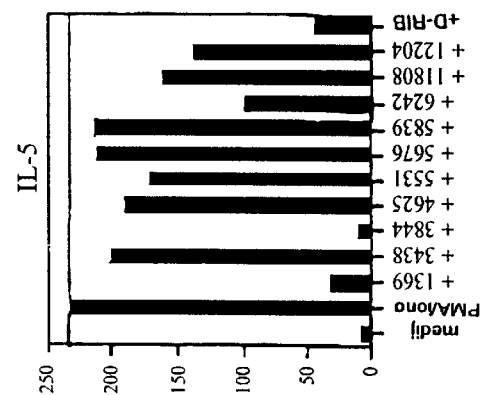
FIG. 7E is a graph showing the results of various concentrations of Ribavirin analogs on IL-5.
Figure 7A:
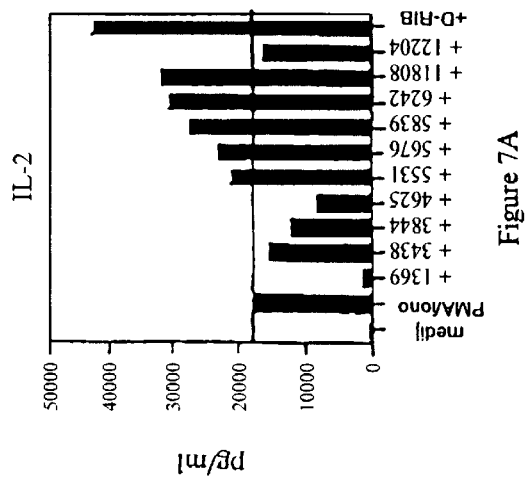
FIG. 7A is a graph showing the results of various concentrations of Ribavirin analogs on IL-2.
Figure 7D:
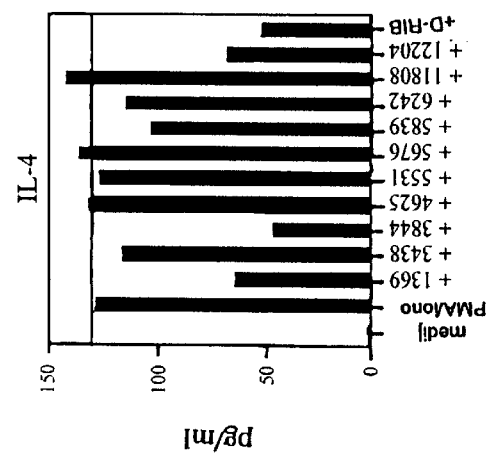
FIG. 7D is a graph showing the results of various concentrations of Ribavirin analogs on IL-4.

Effect of Ribavirin on Intracellular IL-2 Levels In CD4 and CD8+ Subsets of Activated T Cells We examined whether the effect of ribavirin on IL-2 expression was specific to CD4+ or CD8+ T cells. Intracellular IL-2 expression in fixed and Permeabilized activated T cells was determined by two-color flow cytometry using fluorescence-labeled antibodies to CD4 or CD8 and to IL-2. FIG. 5 shows that following treatment with ribavirin at 10 μM, the percentage of CD4+ T cells expressing IL-2 rose from 82 to 91% and the percentage of CD8+ expressing IL-2 increased from 81 to 91%. In contrast, the percentage of IL-2-expressing CD4+ and CD8+ cells following interferon-α-treatment (5000 U/ml) was 81 and 71% respectively. These data suggest ribavirin has an effect on intracellular IL-2 expression which does not discriminate between CD4+ or CD8+ T cell subsets. In contrast, interferon-α-treatment has little effect on CD4+ T cells and even reduces IL-2 expression in the CD8+ T cell subset.

Table 1. The data represents the resting and PMA/ionomycin-activated levels, at 48 and 72 h, of the lymphokines, IL-2, IL-4, TNFα and IFNγ(pg/ml) measured in extracellular supernatants and the cell surface expression of IL-2 (IL-2R) and IL-4 (IL-4R) receptors (mean channel fluorescence intensity) from human T cells.

TABLE 1

|  | 48 h Resting | 48 h Activated | 72 h Resting | 72 h Activated |
|---|---|---|---|---|
| IL-2 | 6.7 (5–9.3) | 1652 (848–2148) | 5.8 (5–9.3) | 1462 (918–1866) |
| IL-4 | 7.5 (7.1–8.2) | 209 (81–363) | 8.5 (7.2–9.2) | 131 (121–148) |
| TNFα | 11.5 (5–18) | 1573 (1474–1672) | 8.3 (5–12) | 1894 (1240–2548) |
| IFNγ | 8.9 (8.3–9.5) | 1285 (807–1765) | 9.3 (9.1–9.4) | 2229 (1230–3228) |
| IL-2R | 50.1 (40.6–59.7) | 163 (160.9–166.5) | 60.1 (49.8–70.4) | 163 (160.1–165.5) |
| IL-4R |  |  | 52.3 (42.6–59.2) | 77.7 (73.5–82.1) |

What is claimed is:

1. A method of treating a disease responsive to ribavirin, comprising:
   recognizing progression of the disease as being mediated at least in part by Th1 lymphocytes;
   recognizing ribavirin as being effective to promote a Th1 response and suppress a Th2 response when administered in a dosage range below which both Th1 and Th2 responses are suppressed; and
   administering ribavirin to a patient having the disease within the dosage range.

2. The method of claim 1 wherein the disease comprises Hepatitis C.

3. The method of claim 1 wherein the dosage range is approximately 4.5 mg/kg of the patient's body weight per day.

4. The method of claim 1 wherein the dosage range achieves a blood serum level in the patient averaging approximately 0.25–6.7 μg/ml of ribavirin.

5. The method of claim 1 wherein the disease comprises Hepatitis C and the dosage range achieves a blood serum level in the patient averaging approximately 0.25–6.7 μg/ml of ribavirin.

6. The method of claim 1 wherein the disease is selected from the group consisting of allergic asthma, atopic dermatitis, helminth infection and leishmaniasis.

7. The method of claim 1 wherein the disease is a primary or secondary immunodeficiency disease.

8. The method of claim 1 wherein promotion of the Th1 response is characterized by increasing production of interleukin 2 (IL-2), tumor necrosis factor (TNFα) and interferon gamma (IFN-γ).

9. The method of any of claims 1–7 further comprising administering interferon alpha to the patient.

* * * * *